(12) United States Patent  
Oliveira

(10) Patent No.: US 8,366,757 B2  
(45) Date of Patent: Feb. 5, 2013

(54) FOAM PAD WITH FAR-INFRARED AND/OR ION GENERATING PROPERTIES AND METHOD FOR PRODUCING IT

(76) Inventor: Arthur Gregory Oliveira, Rockaway, NJ (US)

(*) Notice: Subject to any disclaimer, the term of this patent is extended or adjusted under 35 U.S.C. 154(b) by 1631 days.

(21) Appl. No.: 11/357,864

(22) Filed: Feb. 21, 2006

(65) Prior Publication Data

US 2007/0198070 A1    Aug. 23, 2007

(51) Int. Cl.
*A61F 7/00* (2006.01)
*A47G 9/06* (2006.01)

(52) U.S. Cl. .................. 607/96; 607/108; 5/417; 5/420; 53/524

(58) Field of Classification Search .................. 607/96, 607/108–112; 5/417–421; 53/524
See application file for complete search history.

(56) References Cited

U.S. PATENT DOCUMENTS

| | | | | |
|---|---|---|---|---|
| 4,680,822 A * | 7/1987 | Fujino et al. | ...................... | 5/421 |
| 5,630,961 A * | 5/1997 | Salee | ............................. | 219/759 |
| 5,787,525 A * | 8/1998 | Sugihara et al. | .................. | 5/421 |
| 2005/0076435 A1* | 4/2005 | Kim et al. | ............................. | 5/1 |
| 2009/0035557 A1* | 2/2009 | Hartmann et al. | ............ | 428/331 |
| 2009/0215362 A1* | 8/2009 | Thysell | ........................... | 451/41 |

* cited by examiner

*Primary Examiner* — Ahmed Farah

(57) ABSTRACT

The present invention relates to a foam pad containing far-infrared and/or ion generating particles and method for producing such foam material. The method for producing the foam pad consists of mixing fine particles of a far-infrared and/or ion emitting stone into the base material prior to further processing such as forming, molding or extruding the material. Alternatively, the fine particles of far-infrared and/or ion generating stone may be mixed with an adhesive and used as a coating on the foam pad. The stone generating far-infrared radiation and/or ions is preferably from the group consisting of tourmaline, granite porphyry, quartz porphyry, zeolite, perlite, serpentine, or mixture thereof.

11 Claims, 1 Drawing Sheet

FOAM PAD WITH FAR-INFRARED AND/OR ION GENERATING PROPERTIES AND METHOD FOR PRODUCING IT

BACKGROUND OF INVENTION

The present invention relates to a novel foam pad for use as a yoga mat, exercise mat, mattress pad, seat cushion, pillow, body pad or body wrap. By adding or mixing a finely pulverized powder of far-infrared and/or ion generating stone into a base material prior to processing such material, the resulting finished product provides for unique health promoting benefits.

Other inventions, mainly out of Japan, have incorporated the use of far-infrared producing materials by mixing these powders with synthetic fibers to form a special yarn for creation of clothing, adding these powders to hard plastics to create discs for odor neutralization or EMF reduction or adding the powders to coatings to spray on walls or other construction material. Additionally, these powders have been used in mattress pads by either sandwiching a layer of stone powder between layers of other material or by applying plastic discs incorporating tourmaline onto the surface of the pad.

There is a significant body of literature indicating that far-infrared and/or ion generating materials provide for anti-bacterial and deodorizing effects and provides for an overall invigorating and regenerative effect. Additionally, research in Japan has shown far-infrared stone powder helps improve circulation, aid in stress relief, speed recovery from fatigue and injury and increase mental alertness. The inventor believes these effects are specifically useful when the body is in close contact with the material and/or when a greater sense of relaxation or wellness is desired. For this reason, these effects are very well suited to the products stated in the claims, such as a yoga mat, massage table pad or meditation cushion.

The inventor is not aware of any application were the stone powder of far-infrared and/or ion generating material is actually mixed into a base material of a foam prior to the forming or further processing so that the powder becomes integral to the foam material. The inventor believes there are many advantages to mixing or blending said stone powder directly into the base material or resin prior to processing or forming of the pad. These advantages include but are not limited to ease of processing, improved wear over coatings, ability to maintain flexibility and even consistency of foam, no shifting or movement of stone material, even distribution of powder throughout the material, and improved performance through exposing more surface area of the finely powdered stone. Alternatively, an outer coating may be desirable in the case where expected wear is minimal and/or where the process of adding powder to the base material is undesirable from a cost, manufacturing or performance standpoint.

SUMMARY OF INVENTION

While conventional foam pads are used for a multitude of purposes, no foam pads incorporating far-infrared and/or ion generating stone powder blended into the material have been marketed. The incorporation of the far-infrared and/or ion generating stone powder into the foam pad provides for various health promoting benefits including improved circulation, aiding in stress relief, speeding recovery from fatigue and injuries and increasing mental alertness.

An object of the present invention is to provide a novel foam pad which can be used as a yoga mat, exercise mat, bed pad, pillow, seat cushion, body pad or body wrap which generate far-infrared and/or ion emissions and serves to promote the health of the user.

The present invention provides a method of producing the health promoting foam pad, which method comprises producing a foam pad by blending or adding finely pulverized powder of a stone or stones generating far-infrared and/or ions into the base material or resin prior to processing through standard techniques such as forming, molding, extruding and other common practices of foam production.

Preferably, the foam material is selected from among rubber, neoprene, PVC, polyurethane, polyethylene or visco-elastic foam depending on the final product. Preferably, the finely ground far-infrared and/or ion generating stone is selected from the group consisting of tourmaline, granite porphyry, quartz porphyry, zeolite, perlite, serpentine, or mixture thereof with a particle size of 0.05 to 30 microns and from 0.01 to 20% by weight of final product.

DESCRIPTION OF THE PREFERRED EMBODIMENT

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the claims.

Figure 1:
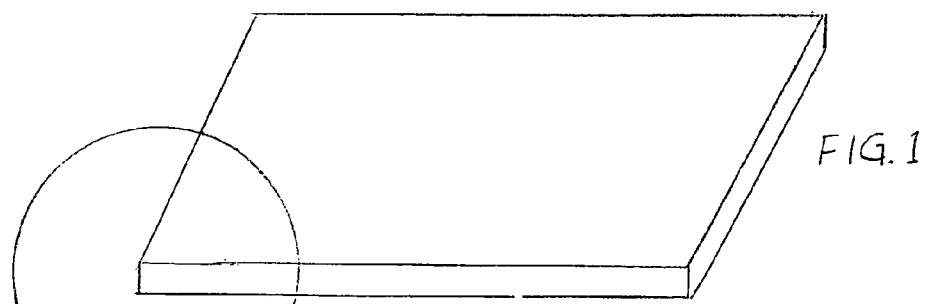
FIG. 1 is a perspective view of the foam pad.
Figure 2:
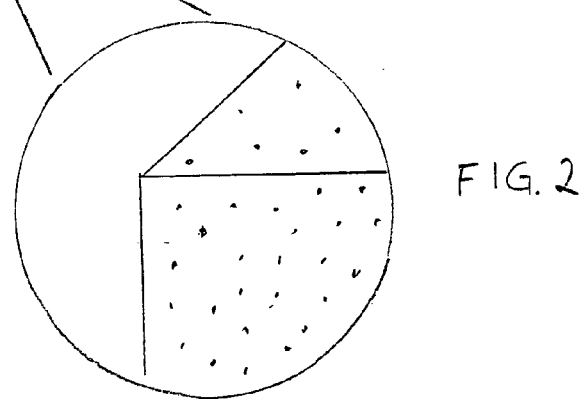
FIG. 2 is a cross-sectional view of a portion of the foam pad showing a fine dispersion of far-infrared and/or ion generating stone powder.
Figure 3:
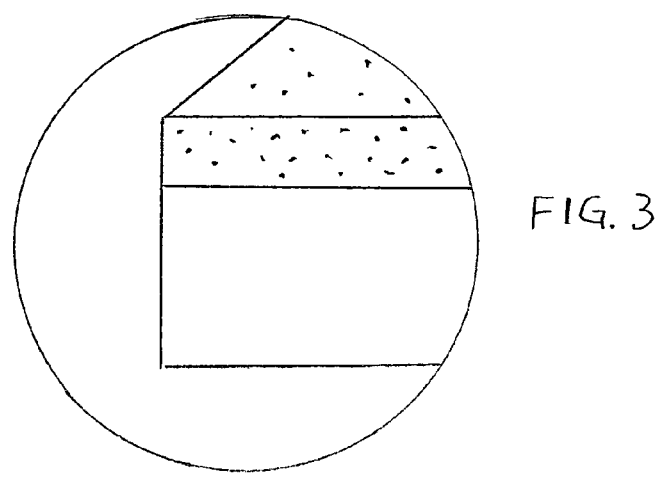
FIG. 3 is a cross-sectional view of a portion of the foam pad showing a fine dispersion of far-infrared and/or ion generating stone powder in the upper layer of a multi-layer foam pad.

The present invention includes a foam pad in the shape and form of a yoga mat or exercise mat (FIG. 1). The pad can be made up of PVC, natural rubber or any other foam type material suitable for use as a yoga or exercise mat. Within the foam structure are finely ground particles of far-infrared and/or ion generating stone (FIG. 2). The preferred stone would come from the group consisting of tourmaline, granite porphyry, quartz porphyry, zeolite, perlite, serpentine, or mixture thereof with a particle size of 0.05 to 30 microns and from 0.01 to 20% by weight. The stone powder will be mixed or blended with the base material prior to forming, molding or extruding into the desired shape and texture. The foam pad may also be formed in layers so as to allow for just a top layer of the construction to contain the fine powder of far-infrared and/or ion generating stone (FIG. 3).

Figure 4:
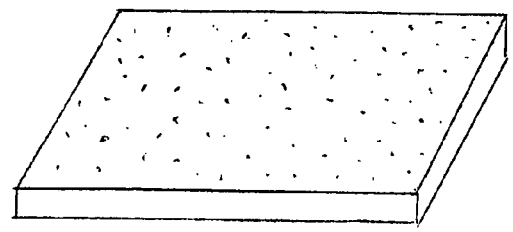
FIG. 4 is a perspective view of the foam pad showing an outer coating or surface treatment having a fine dispersion of far-infrared and/or ion generating stone powder as the key ingredient of said coating.

In an alternative embodiment the invention includes a foam pad with a surface coating containing fine powder of a far-infrared and/or ion generating stone mixed with an adhesive or other binding agent (FIG. 4). This coating or surface treatment may be applied to the formed or molded product by spraying, brushing, dipping or other common application method. A solvent or other additive may be included in the mixture to provide for improved application or wear characteristics.

What is claimed is:

1. A foam pad providing therapeutic benefits, the foam pad comprising:
   a base material, said base material being rubber, neoprene, PVC, polyurethane, visco-elastic foam or other synthetic resin; and
   a fine powder, said powder including far-infrared and/or ion generating stone material;
   wherein said fine powder is dispersed and intermingled with said base material.

2. The foam pad of claim 1 wherein foam pad is formed for the purpose of acting as a yoga mat, Pilates mat or exercise mat.

3. The foam pad of claim 1 wherein foam pad is formed for the purpose of acting as a body pad or wrap such as a knee pad, elbow wrap or foot pad.

4. The foam pad of claim 1 wherein foam pad is formed for the purpose of acting as a seat cushion or meditation cushion.

5. The foam pad of claim 1 wherein foam pad is formed for the purpose of acting as a pad for a massage table.

6. The foam pad of claim 1 wherein foam pad is formed for the purpose of acting as a mattress pad.

7. The foam pad of claim 1 wherein foam pad is formed for the purpose of acting as a pillow.

8. The foam pad of claim 1 wherein said far-infrared and/or ion generating stone powder is selected from the group consisting of tourmaline, granite porphyry, quartz porphyry, zeolite, perlite, serpentine, or mixture thereof.

9. The foam pad of claim 1 wherein said fine powder further contains fine particles of other inorganic material which emit far-infrared and/or ion generating properties and/or amplify the effects of such material including but not limited to alumina, ferrite, copper, chromium oxide, titanium oxide, zircon and silica.

10. The foam pad of claim 1 wherein the foam pad contains other additives which provide an anti-mold, anti-fungal, deodorizing, or scented effect.

11. The foam pad of claim 1, comprising at least two layers and wherein said fine powder and said base material form at least one layer of said at least two layers.

* * * * *